US010196621B2

(12) United States Patent
Kim et al.

(10) Patent No.: US 10,196,621 B2
(45) Date of Patent: Feb. 5, 2019

(54) *ACANTHOPHYSIUM* SP. KMF001 HAVING HIGH CELLULASE ACTIVITY (71) Applicant: Kookmin University Industry Academy Cooperation Foundation, Seoul (KR)

(72) Inventors: Yeong-Suk Kim, Gyeonggi-do (KR); Tae-Jong Kim, Seoul (KR); Keum Shin, Seoul (KR); Sae Min Yoon, Gyeonggi-do (KR)

(73) Assignee: Kookmin University Industry Academy Cooperation Foundation, Seoul (KR)

( * ) Notice: Subject to any disclaimer, the term of this patent is extended or adjusted under 35 U.S.C. 154(b) by 0 days.

(21) Appl. No.: 14/930,585

(22) Filed: Nov. 2, 2015

(65) Prior Publication Data

US 2017/0121698 A1    May 4, 2017

(51) Int. Cl.
*C12N 9/42* (2006.01)
*C12N 1/14* (2006.01)
*D21B 1/02* (2006.01)
*C12R 1/645* (2006.01)

(52) U.S. Cl.
CPC ............ *C12N 9/2437* (2013.01); *C12N 1/14* (2013.01); *C12N 9/2445* (2013.01); *C12R 1/645* (2013.01); *D21B 1/021* (2013.01); *C12Y 302/01004* (2013.01); *C12Y 302/01021* (2013.01)

(58) Field of Classification Search
CPC ...... C12N 9/2437; C12N 1/14; C12N 9/2445; C12R 1/645; D21B 1/021; C12Y 302/01021; C12Y 302/01004
See application file for complete search history.

(56) References Cited

U.S. PATENT DOCUMENTS

| 4,677,198 A * | 6/1987 | Linnett | C13K 13/00 530/500 |
| 2002/0164727 A1* | 11/2002 | Kishimoto | C07D 333/34 435/118 |
| 2005/0067347 A1* | 3/2005 | Vanhulle | C02F 1/78 210/606 |
| 2007/0172938 A1* | 7/2007 | Deguchi | C08L 1/02 435/253.6 |
| 2013/0316055 A1* | 11/2013 | Holt | A23B 4/10 426/332 |

FOREIGN PATENT DOCUMENTS

KR    10-2010-0125845 A    12/2010

OTHER PUBLICATIONS

Viswanath, B et al. Screening and assessment of laccase producing fungi isolated from different environmental samples. 2008. 7(8): 1129-1133.*
Shim, K., et al, "Biopolishing fibers using biocatalysts from a wood rotting fungus KMF001", 2015 Proceeding of the Korean Society of Wood Science and Technology Annual Meeting, Kangwon National University, Chuncheon, Korea, Apr. 10, 2015, pp. 462-463 (English Abstract; Partial English Translation—Tables).
Yoon, S., et al., "The pretreatment effect of biocatalysts from a wood rotting fungus KMF001 on nano-cellulose production", 2015 Proceeding of the Korean Society of Wood Science and Technology Annual Meeting, Kangwon National University, Chuncheon, Korea, Apr. 10, 2015, pp. 310-311 (English Abstract).
Kim, Y., et al., "A high cellulase activity of Acanthophysium sp. KMF001", Nov. 5-6, 2014, pp. 155-162 (Abstract), The International Symposium on the High-Intensity Utilization of Forest Biomaterials, Kangwon National University, Chuncheon, Korea.
Kim, Y., et al., "Enzymatic saccharification of lignocellulosic biomass using highly active extracellular enzymes of a wood rotting fungus", Apr. 16-17, 2015, p. 1 (English Abstract), 2015 the Annual Meeting of Korean Forest Bioenergy Society, 2015 Ramada Plaza Jeju, Jeju, Korea.
King, B., et al., "An Optimized Microplate Assay System for Quantitative Evaluation of Plant Cell Wall-Degrading Enzyme Activity of Fungal Culture Extracts", "Biotechnology and Bioengineering", Sep. 29, 2008, pp. 1033-1044, vol. 102, No. 4.
Shin, K., et al., "Biopolishing fibers using biocatalysts from a wood rotting fungus KMF001", Apr. 10-11, 2015, pp. 462-463 (Abstract) (Partial English Translation), 2015 Proceeding of the Korean Society of Wood Science and Technology Annual Meeting, Kangwon National University, Chuncheon, Korea.
Yoon, S., et al., "Screening new glycoside hydrolase genes from Acanthophysium sp. KMF001", Mar. 16-18, 2015, pp. N17-P-F08 (English Abstract), The 65th Annual Meeting of the Japan Wood Research Society, Tower Hall Funabori, Tokyo, Japan.
Yoon, S., et al., "The pretreatment effect of biocatalysts from a wood rotting fungus KMF001 on nano-cellulose Production", Apr. 10-11, 2015, pp. 310-311 (Abstract), 2015 Proceeding of the Korean Society of Wood Science and Technology Annual Meeting, Kangwon National University, Chuncheon, Korea.

* cited by examiner

*Primary Examiner* — Renee Claytor
*Assistant Examiner* — Susan E. Fernandez
(74) *Attorney, Agent, or Firm* — Hultquist, PLLC; Steven J. Hultquist (57) ABSTRACT

The present invention relates to *Acanthophysium* sp. KMF001 strain having high cellulose activity, and more particularly, to a novel *Acanthophysium* sp. KMF001 strain having the ability to produce endo-β-1,4-glucanase, β-glucosidase, and cellobiohydrolase and to a culture of the strain. The novel *Acanthophysium* sp. KMF001 strain according to the present invention can produce highly active cellulases, including endo-β-1,4-glucanase, β-glucosidase, and cellobiohydrolase, and thus can be advantageously used not only for enzymatic saccharification of lignocellulosic biomass, but also in various industrial fields, including the pulp and paper making industry, the detergent industry, the agricultural product processing industry, the fiber industry, and the livestock industry, in which the degradation of cellulose is required.

5 Claims, 6 Drawing Sheets

Specification includes a Sequence Listing.

ACANTHOPHYSIUM SP. KMF001 HAVING HIGH CELLULASE ACTIVITY

TECHNICAL FIELD

The present invention relates to *Acanthophysium* sp. KMF001 strain having high cellulose activity, and more particularly, to novel *Acanthophysium* sp. KMF001 strain having the ability to produce endo-β-1,4-glucanase, β-glucosidase, and cellobiohydrolase, and to a culture of the strain.

BACKGROUND ART

Advanced countries, including the USA and the EU, announced that the consumption of gasoline will be reduced by 20-30% and the use of biofuels will be increased during the year 2017-2030. At present, the USA and Brazil produce bioethanol from their abundant biomass such as maize or sugar cane and commercially use it as an alternative fuel for transportation in considerable amounts.

According to the report of the Korea Bio-Energy Association, it was estimated that the amount of waste cooking oil used in the production of biodiesel reached 120,000 tons in the year 2012 and 153,000 tons in the year 2013. Thus, nonfood biomass such as lignocellulosic biomass is emerging as a next-generation raw material for energy production, and the attention on the production of biofuels from lignocellulosic biomass has never been higher. Lignocellulosic biomass has advantages in the size of annual production, about 10-50 billion tons per year, and its renewability, but has disadvantages in the slow growth rate and the difficult degradation of cellulose bound to lignin. To overcome such disadvantages, the development of highly efficient cellulase is essential. Furthermore, it is expected that the commercial market size of cellulase will be expanded rapidly within 5-10 years. According to the Korean Journal of Mycology in 2012, cellulase used in the production of bioenergy was 11% of the global industrial enzyme market, and thus the value of cellulases is newly emerging and expanding.

Cellulases are produced on a pilot or commercial scale by use of strains such as *Trichoderma reesei*, *Penicillium funiculosum*, and *Aspergillus niger*. In addition, cellulases are also produced from bacteria, including *Acidothermus cellulolyticus*, *Micromonospora bispora*, *Bacillus* sp., *Cytophaga* sp., *Streptomyces stercorarium*, *Clostridium thermocellum*, and *Ruminococcus albus*.

*Trichoderma reesei* is a well-known cellulase producer, and its cellulases have advantages in high stability under enzymatic saccharification conditions and high resistance against chemical inhibitors, but have a disadvantage of low β-glucosidase (BGL) activity (Brian et al, *Biotechno. Bioeng.* 102:1033-1044, 2009).

The present inventors have made extensive efforts to develop a novel strain having the ability to produce highly active cellulase. As a result, the present inventors have isolated novel *Acanthophysium* sp. KMF001 strain, and have found that the isolated strain produces cellulases having activities higher than those of conventional strains, thereby completing the present invention.

DISCLOSURE OF INVENTION

It is an object of the present invention to provide *Acanthophysium* sp. KMF001 strain having the ability to produce highly active cellulase, and a culture of the strain.

Another object of the present invention is to provide a method of producing cellulase by culture of the strain, and *Acanthophysium* sp. strain-derived cellulase produced by the method.

Still another object of the present invention is to provide a method of degrading cellulose by use of *Acanthophysium* sp. KMF001 strain, the cellulase, or a culture of the strain.

To achieve the above objects, the present invention provides *Acanthophysium* sp. KMF001 strain (KCTC 18282P) having the ability to produce highly active cellulase.

The present invention also provides a method for producing cellulase, comprising the steps of: (a) culturing *Acanthophysium* sp. strain to produce cellulase; and (b) recovering the produced cellulase.

The present invention also provides a cellulase produced by the method, and a culture of the strain, which has cellulase activity.

The present invention also provides a method for degrading cellulose, which comprises using the strain, the cellulase, or a culture of the strain.

Advantageous Effects

The novel *Acanthophysium* sp. KMF001 strain according to the present invention can produce highly active cellulases, including endo-β-1,4-glucanase, β-glucosidase, and cellobiohydrolase, and thus can be advantageously used not only for enzymatic saccharification of lignocellulosic biomass, but also in various industrial fields, including the pulp and paper making industry, the detergent industry, the agricultural product processing industry, the fiber industry, and the livestock industry.

BEST MODE FOR CARRYING OUT THE INVENTION

In the present invention, the activities of three different cellulases (EG, BGL, and CBH) in 54 strains known as wood-rotting fungi were measured, and based on the measurements, *Acanthophysium* sp. KMF001 showing the highest cellulase activities was isolated.

The 28S rRNA nucleotide sequence of the isolated strain was analyzed, and as a result, it was found that the isolated strain has a nucleotide sequence of SEQ ID NO: 1. In addition, the nucleotide sequence of the isolated strain was compared with those of reported strains, and as a result, the isolated strain was identified to be the genus of *Acanthophysium*. The isolated strain was named "*Acanthophysium* sp. KMF001", and deposited with the Korean Collection for Type Cultures (KCTC), the Biological Resource Center (BRC), the Korea Research Institute of Bioscience and Biotechnology (KRIBB) 181, Ipsin-gil, Jeongeup-si, Jeollabuk-do 56212, Republic of Korea, on Apr. 21, 2014 under Accession No. KCTC 18282P, and such deposit was converted on Oct. 10, 2016 to a deposit under the Budapest Treaty on the International Recognition of the Deposit of Microorganisms for the Purpose of Patent Procedure, with Accession No. KCTC 13124BP.

The genetic relationship of *Acanthophysium* sp. KMF001 with similar species was analyzed using the 28S rRNA nucleotide sequence of *Acanthophysium* sp. KMF001. As a result, it was found that *Acanthophysium* sp. KMF001 showed a homology of 90% to *Acanthophysium lividocaeruleum*, *Acanthophysellum lividocaeruleum*, *Xylobolus frustulatus*, and *Xylobolus subpileatus*.

Thus, in one aspect, the present invention is directed to *Acanthophysium* sp. KMF001 strain (KCTC 18282P) having the ability to produce highly active cellulase.

In the present invention, *Acanthophysium* sp. KMF001 strain may have a 28S rRNA nucleotide sequence of SEQ ID NO: 1.

In the present invention, the cellulase may be selected from the group consisting of endo-1,4-glucanase, glucosidase, and cellobiohydrolase.

In an example of the present invention, *Acanthophysium* sp. KMF001 strain was cultured, and as a result, it was found that the cellulase secreted into media and a culture of the strain had higher cellulase activity than those of conventional strains.

Thus, in another aspect, the present invention is directed to a method for producing cellulase, comprising the steps of: (a) culturing *Acanthophysium* sp. strain to produce cellulase; and (b) recovering the produced cellulase, and a cellulase produced by the method.

In the present invention, the culture may be performed in a medium containing the following: a carbon source selected from the group consisting of cellulose, glucose, lactose, cellobiose, carboxymethyl cellulose (CMC) sodium salt, xylan, rice-straw, avicel, and acorns; a nitrogen source selected from the group consisting of peptone, yeast extract, trypton, corn steep powder, urea, a 2:8 mixture of yeast and peptone, and a 7:3 mixture of trypton and yeast; potassium dihydrogen phosphate ($KH_2PO_4$); potassium hydrogen phosphate ($K_2HPO_4$); and magnesium sulfate ($MgSO_4.7H_2O$). In addition, the culture may be performed at a pH of 5.5-6.5 and a temperature of 22 to 28° C.

In an example of the present invention, it was found that a culture of the strain degraded cellulose while having highly active endo-1,4-glucanase, β-glucosidase and cellobiohydrolase.

Thus, in yet another aspect, the present invention is directed to a method for degrading cellulose, which comprises using the strain, the cellulase, or a culture of the strain.

As used herein, the term "cellulose" is intended to include not only cellulose itself, but also cellulose-containing materials, including rice-straw, lignocellulosic biomass, glucose, lactose, cellobiose, carboxymethyl cellulose (CMC) sodium salt, xylan, avicel, and acorns.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Isolation of Strains

The total 54 strains known as wood-rotting fungi were isolated from deteriorated wood. To select a strain, which produce highly active cellulases, the activities of endo-β-1, 4-glucanase (EG), β-glucosidase (BG) and cellobiohydrolase (CBH) of isolated strains were measured in the same manner as described in Example 4, and based on the measurement results, a strain selection was performed. As shown in Tables 3 to 5, the results of measurement of the cellulase activities indicated that the EG activity was the highest in T. KONINGII (5.58 U/L) and was higher in the order of GAN (5.46 U/L), TRR (4.70 U/L), LAS (4.60 U/L), SSU (3.82 U/L), and TRV-2 (3.42 U/L). However, in the case of GAN showing the second highest EG activity, BGL and CBH activities were remarkably low. The BGL activity was the highest in PEC (11 U/L), but the EG activity in PEC was remarkably low too. In addition, SSU showed high BGL activity (10.96 U/L), and LAS, TRV-2, T.KONINGII, and PPE also showed high BGL activity (10.7-10.9 U/L). The CBH activity was the highest in SSU (11.14 U/L) and PPE (11.08 U/L). Among the 54 strains used in the strain selection experiment, 7 strains including SSU, PPE, and PAE showed relatively high cellulase activity. Among the selected 7 strains, SSU showed the highest enzymatic activity. Table 2 below is a list of 54 strains used in the strain selection experiment, and Table 1 below shows the cellulase activities of 7 strains having high cellulase activities, selected from the 54 strains.

TABLE 1

| No. | Fungi | EG (U/L) | BGL (U/L) | CBH (U/L) |
|---|---|---|---|---|
| 29 | SSU | 3.82 | 10.96 | 11.14 |
| 27 | PPE | 3.22 | 10.76 | 11.08 |
| 26 | PAE | 1.70 | 3.76 | 0.24 |
| 50 | T. KONINGII | 5.58 | 10.8 | 6.6 |
| 30 | LAS | 4.60 | 10.94 | 10.6 |
| 49 | TRR | 4.70 | 8.5 | 1.04 |
| 28 | TRV-2 | 3.42 | 10.84 | 0.34 |

TABLE 2

| No. | Fungi |
|---|---|
| 1 | PAR |
| 2 | DAD-A |
| 3 | GLR |
| 4 | DAD-B |
| 5 | TRH |
| 6 | PEC |
| 7 | ASN-2 |
| 8 | CRB |
| 9 | GAL |
| 10 | STH |
| 11 | CRC |
| 12 | ASV |
| 13 | GRF |
| 14 | TRV-3 |
| 15 | CPU |
| 16 | LEE |
| 17 | GAL |
| 18 | SEL-2 |
| 19 | LAV |
| 20 | HEC |
| 21 | POC |

TABLE 2-continued

| No. | Fungi |
|---|---|
| 22 | COV |
| 23 | FOA |
| 24 | FOP |
| 25 | FOF |
| 26 | PAE |
| 27 | PPE |
| 28 | TRV-2 |
| 29 | SSU |
| 30 | LAS |
| 31 | GAN |
| 32 | PRH |
| 33 | PLC |
| 34 | PCT |
| 35 | PAT |
| 36 | PFA |
| 37 | STB |
| 38 | COP-2 |
| 39 | Fpi001 |
| 40 | Fpi002 |
| 41 | CHG |
| 42 | ASN-1 |
| 43 | COP-1 |
| 44 | PLE |
| 45 | GAB001 |
| 46 | SEL-1 |
| 47 | Fpa |
| 48 | *A. PRAECOX* |
| 49 | TRR |
| 50 | *T. KONINGII* |
| 51 | T. OBLO. |
| 52 | RHN |
| 53 | PEC |
| 54 | TRV-1 |

TABLE 3

| No. | Fungi | EG (U/L) |
|---|---|---|
| 50 | *T. KONINGII* | 5.58 |
| 31 | GAN | 5.46 |
| 49 | TRR | 4.70 |
| 30 | LAS | 4.60 |
| 29 | SSU | 3.82 |
| 28 | TRV-2 | 3.42 |
| 27 | PPE | 3.22 |
| 26 | PAE | 1.70 |
| 25 | PAE | 1.64 |
| 48 | *A. PRAECOX* | 1.00 |
| 24 | FOP | 0.88 |
| 23 | FOA | 0.86 |
| 46 | SEL-1 | 0.86 |
| 47 | Fpa | 0.86 |
| 22 | COV | 0.84 |
| 45 | GAB001 | 0.84 |
| 21 | POC | 0.82 |
| 19 | LAV | 0.78 |
| 20 | HEC | 0.78 |
| 17 | GAL | 0.76 |
| 18 | SEL-2 | 0.76 |
| 15 | CPU | 0.74 |
| 16 | LEE | 0.74 |
| 44 | PLE | 0.72 |
| 14 | TRV-3 | 0.66 |
| 43 | COP-1 | 0.66 |
| 12 | ASV | 0.6 |
| 13 | GRF | 0.6 |
| 11 | CRC | 0.58 |
| 40 | Fpi002 | 0.58 |
| 10 | STH | 0.56 |
| 41 | CHG | 0.56 |
| 9 | GAL | 0.54 |
| 8 | CRB | 0.50 |
| 6 | PEC | 0.48 |
| 38 | COP-2 | 0.48 |
| 5 | TRH | 0.44 |

TABLE 3-continued

| No. | Fungi | EG (U/L) |
|---|---|---|
| 4 | DAD-B | 0.34 |
| 3 | GLR | 0.32 |
| 2 | DAD-A | 0.30 |
| 7 | ASN-2 | 0.24 |
| 39 | Fpi001 | 0.20 |
| 1 | PAR | 0.20 |
| 32 | PRH | N.D. |
| 33 | PLC | N.D. |
| 34 | PCT | N.D. |
| 35 | PAT | N.D. |
| 36 | PFA | N.D. |
| 37 | STB | N.D. |
| 42 | ASN-1 | N.D. |
| 51 | T. OBLO. | N.D. |
| 52 | RHN | N.D. |
| 53 | PEC | N.D. |
| 54 | TRV-1 | N.D. |

[1]N.D.: Not Detected

TABLE 4

| No. | Fungi | BGL (U/L) |
|---|---|---|
| 53 | PEC | 11 |
| 29 | SSU | 10.96 |
| 30 | LAS | 10.94 |
| 28 | TRV-2 | 10.84 |
| 50 | *T. KONINGII* | 10.8 |
| 27 | PPE | 10.76 |
| 1 | PAR | 9.38 |
| 49 | TRR | 8.5 |
| 36 | PFA | 8.42 |
| 35 | PAT | 8.16 |
| 42 | ASN-1 | 5.74 |
| 54 | TRV-1 | 5.3 |
| 34 | PCT | 4.86 |
| 26 | PAE | 3.76 |
| 33 | PLC | 2.52 |
| 52 | RHN | 1.06 |
| 31 | GAN | 0.56 |
| 5 | TRH | 0.22 |
| 17 | GAL | 0.22 |
| 51 | T. OBLO. | 0.2 |
| 19 | LAV | 0.2 |
| 41 | CHG | 0.1 |
| 4 | DAD-B | 0.1 |
| 9 | GAL | 0.08 |
| 7 | ASN-2 | 0.06 |
| 32 | PRH | 0.06 |
| 40 | Fpi002 | 0.04 |
| 14 | TRV-3 | 0.04 |
| 39 | Fpi001 | 0.04 |
| 2 | DAD-A | 0.02 |
| 20 | HEC | 0.02 |
| 3 | SEL-2 | 0 |
| 6 | CPU | 0 |
| 8 | STH | 0 |
| 10 | CRB | N.D. |
| 11 | CRC | N.D. |
| 12 | ASV | N.D. |
| 13 | GRF | N.D. |
| 15 | PEC | N.D. |
| 16 | LEE | N.D. |
| 18 | GLR | N.D. |
| 21 | POC | N.D. |
| 22 | COV | N.D. |
| 23 | FOA | N.D. |
| 24 | FOP | N.D. |
| 25 | FOF | N.D. |
| 37 | STB | N.D. |
| 38 | COP-2 | N.D. |
| 43 | COP-1 | N.D. |
| 44 | PLE | N.D. |
| 45 | GAB001 | N.D. |
| 46 | SEL-1 | N.D. |

TABLE 4-continued

| No. | Fungi | BGL (U/L) |
|---|---|---|
| 47 | Fpa | N.D. |
| 48 | *A. PRAECOX* | N.D. |

1)N.D.: Not Detected

TABLE 5

| No. | Fungi | CBH (U/L) |
|---|---|---|
| 29 | SSU | 11.14 |
| 27 | PPE | 11.08 |
| 30 | LAS | 10.6 |
| 53 | PEC | 8.36 |
| 50 | *T. KONINGII* | 6.6 |
| 1 | PAR | 2.92 |
| 36 | PFA | 2.1 |
| 42 | ASN-1 | 1.5 |
| 49 | TRR | 1.04 |
| 35 | PAT | 0.68 |
| 34 | PCT | 0.4 |
| 54 | TRV-1 | 0.34 |
| 33 | PLC | 0.28 |
| 41 | CHG | 0.26 |
| 26 | PAE | 0.24 |
| 4 | DAD-B | 0.08 |
| 31 | GAN | 0.08 |
| 52 | RHN | 0.08 |
| 19 | LAV | 0.06 |
| 20 | HEC | 0.04 |
| 40 | Fpi002 | 0.04 |
| 2 | DAD-A | 0.02 |
| 5 | TRH | 0.02 |
| 7 | ASN-2 | 0.02 |
| 14 | TRV-3 | 0.02 |
| 28 | TRV-2 | 0.02 |
| 51 | T. OBLO. | 0.02 |
| 10 | STH | 0 |
| 32 | PRH | 0 |
| 3 | GLR | N.D. |
| 6 | PEC | N.D. |
| 8 | CRB | N.D. |
| 9 | GAL | N.D. |
| 11 | CRC | N.D. |
| 12 | ASV | N.D. |
| 13 | GRF | N.D. |
| 15 | CPU | N.D. |
| 16 | LEE | N.D. |
| 17 | GAL | N.D. |
| 18 | SEL-2 | N.D. |
| 21 | POC | N.D. |
| 22 | COV | N.D. |
| 23 | FOA | N.D. |
| 24 | FOP | N.D. |
| 25 | FOF | N.D. |
| 37 | STB | N.D. |
| 38 | COP-2 | N.D. |
| 39 | Fpi001 | N.D. |
| 43 | COP-1 | N.D. |
| 44 | PLE | N.D. |
| 45 | GAB001 | N.D. |
| 46 | SEL-1 | N.D. |
| 47 | Fpa | N.D. |
| 48 | *A. PRAECOX* | N.D. |

1)N.D.: Not Detected

Example 2: Identification of Strain

In order to identify the SSU strain isolated in Example 1, the nucleotide sequence of the 28S rRNA gene was analyzed.

(1) gDNA Extraction and PCR gDNA was extracted from the strain isolated in Example 1, followed by PCR.

Specifically, cells of the strain were lysed using a tissue lyser, and then gDNA was extracted therefrom using a Qiagen DNeasy Plant Mini kit. Next, in order to obtain a sufficient amount of DNA required for sequencing, the extracted gDNA was amplified by PCR using the internal transcribed spacer (ITS) primers shown in Table 6 below.

TABLE 6

| Primer name | Sequence(5'->3') | SEQ ID NO: |
|---|---|---|
| ITS4(10 pmole/μL) | TCCTCCGCTTATTGATATGC | 2 |
| ITS5(10 pmole/μL) | GGAAGTAAAAGTCGTAACAAGG | 3 |

Figure 1:
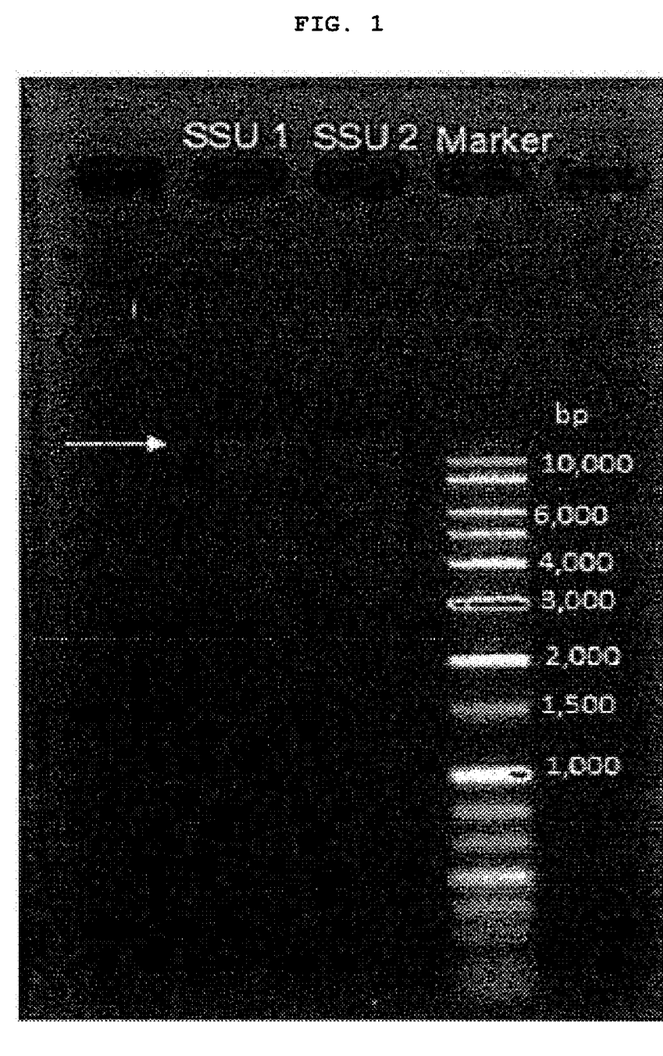
FIG. 1 shows bands obtained from agarose gel electrophoresis of a gDNA extracted from *Acanthophysium* sp. KMF001 strain.
Figure 2:
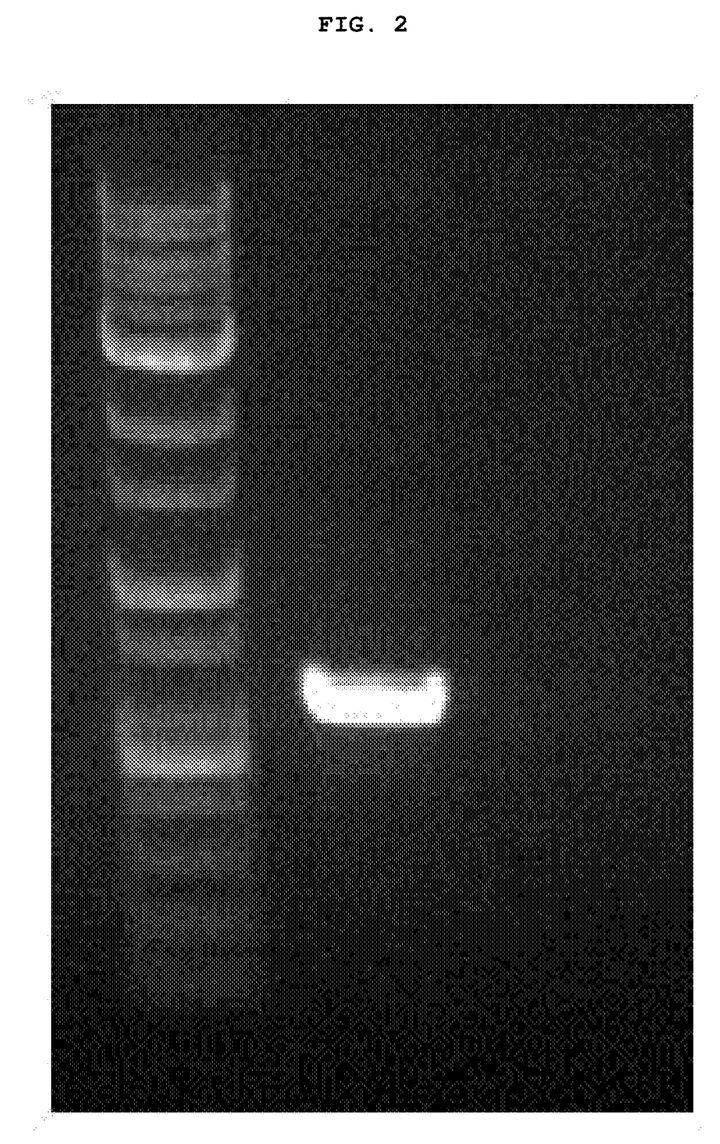
FIG. 2 shows bands obtained from agarose gel electrophoresis of a product obtained by the PCR amplification of the gDNA of *Acanthophysium* sp. KMF001 strain.

As a result, it could be seen that the gDNA showed a faint band slightly above 10,000 bp and that the PCR product showed a single band at a position of about 650 bp (FIGS. 1 and 2). The PCR product was purified and sequenced.

(2) Identification and Nucleotide Sequence Analysis

The 28S rRNA was sequenced by BIOFACT Co., Ltd., and as a result, the SSU strain was identified to be *Acanthophysium* sp. strain. The identified strain was named "*Acanthophysium* sp. KMF001", and deposited with the Korean Collection for Type Cultures (KCTC), the Biological Resource Center (BRC), the Korea Research Institute of Bioscience and Biotechnology (KRIBB), on Apr. 21, 2014 under Accession No. KCTC 18282P.

The 28S rRNA nucleotide sequence of *Acanthophysium* sp. KMF001 strain was checked by NCBI Blast search. As a result, as shown in Table 7 below, *Acanthophysium* sp. KMF001 strain had a homology of 98% to the following five strains: *Acanthophysium lividocaeruleum* (AY039314.1), *Acanthophysellum lividocaeruleum* (AF506400.1), *Xylobolus frustulatus* (AF506491.1), *Acanthophysium lividocaeruleum* (AY039319.1), and *Xylobolus subpileatus* (AY039309.1). Thus, it is believed that *Acanthophysium* sp. KMF001 strain is an unidentified strain which has not yet been reported.

TABLE 7

| Accession | Description | Query coverage | E-value | Max identity |
|---|---|---|---|---|
| AY039314.1 | *Acanthophysium lividocaeruleum* | 99% | 0 | 98% |
| AF506400.1 | *Acanthophysellum lividocaeruleum* | 99% | 0 | 98% |
| AF506491.1 | *Xylobolus frustulatus* | 99% | 0 | 98% |
| AY039319.1 | *Acanthophysium lividocaeruleum* | 99% | 0 | 98% |
| AY039309.1 | *Xylobolus subpileatus* | 99% | 0 | 98% |

(3) Phylogenetic Analysis

Figure 3:
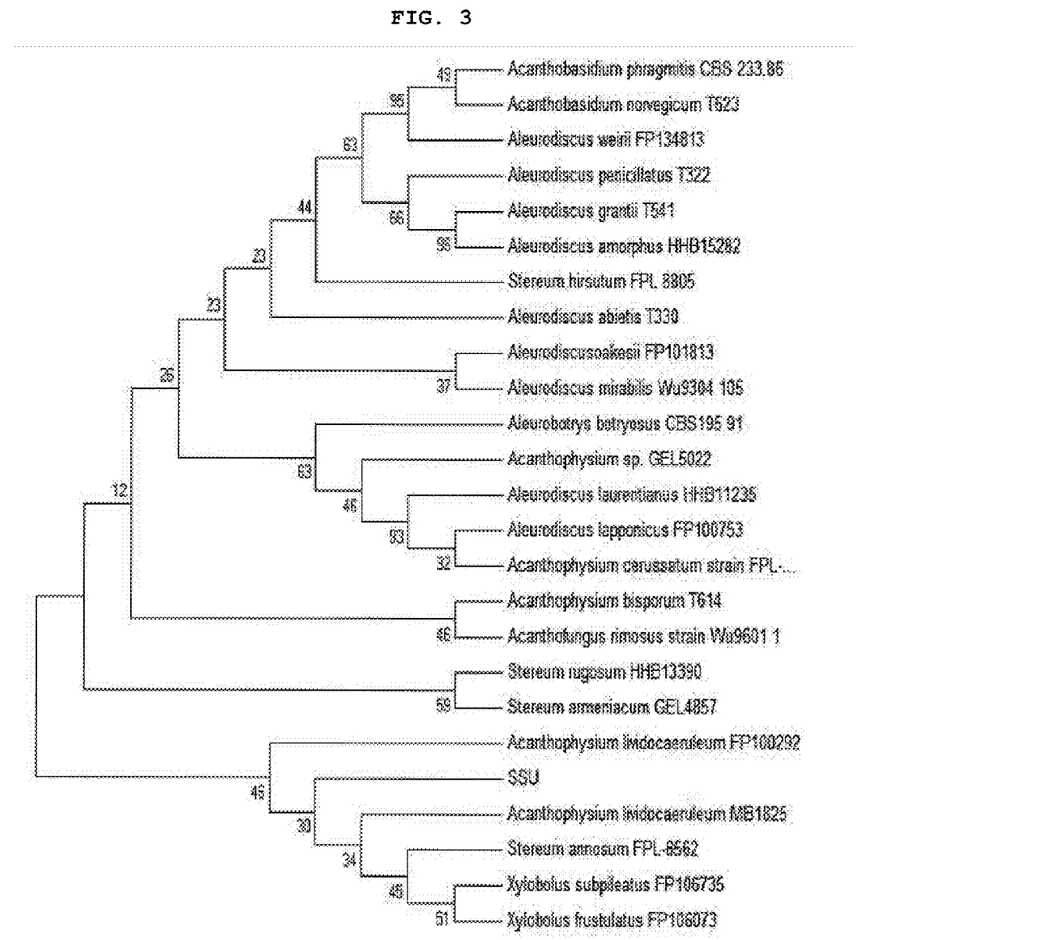
FIG. 3 shows the results of phylogenetic analysis performed using the rDNA of *Acanthophysium* sp. KMF001 strain. SSU represents the *Acanthophysium* sp. KMF001 strain.

The strain identification indicated that, among currently known strains, there are strains similar to the isolated strain, but their similarities are not enough to indicate the same strain. For this reason, the taxonomic position of *Acanthophysium* sp. KMF001 strain was determined through phylogenetic analysis with the strains shown in the identification results. MEGA4 program was used to determine the taxonomic position, and the results are shown in FIG. 3 of phylogenetic analysis performed using the rRNA of each strain. In this method, a distance based on similarity between data is expressed, and sampling is repeated 1000 times to indicate statistical accuracy. The results of the phylogenetic analysis indicated that *Acanthophysium* sp. KMF001 strain branches different from *Acanthophysium lividocaeruleum* strain MB1825 showing an identity of 98.7% in NCBI blast search, suggesting that *Acanthophysium* sp. KMF001 strain is a novel strain which has not yet been registered.

Example 3: Culture of Strain and Collection of Culture

Each of *Acanthophysium* sp. KMF001 strain isolated in Example 1 and control strains (*Trichoderma reesei*, *Fomitopsis palustris*, and *Aspergillus niger*) was cultured in potato dextrose agar (PDA) medium for 3-4 days, and the mycelia were inoculated into 100 mL of potato dextrose broth (PDB) medium and shake-cultured at 22-28° C. and 100-180 rpm for 3-7 days. The shake-cultured strains were used in main culture.

Specifically, for main culture, each of the strains was added to a liquid medium (pH 5.5) having a composition comprising 5-11 g/L of peptone, 2-8 g/L of potassium dihydrogen phosphate ($KH_2PO_4$), 2-8 g/L of potassium hydrogen phosphate ($K_2HPO_4$), 1-5 g/L of magnesium sulfate ($MgSO_4$-$7H_2O$), 1-3 g/L of yeast extract, and 15-25 g/L of cellulose (Aldrich, about 20 micron), and was inoculated with 5% (v/v) of a preculture of each strain, followed by culture at 22-28° C. and 100-200 rpm for 2-3 weeks. During 2-3 weeks of culture, 500 μL of a culture of each strain was collected each day and centrifuged, and the supernatant was separated and used in the measurement of enzymatic activities.

Example 4: Measurement of Cellulase Activities

For measurement of cellulase activities, the activity of endo-β-1,4-glucanase (EG) was measured by the Somogyi-Nelson method using reducing sugar, and the activities of β-glucosidase (BG) and cellobiohydrolase (CBH) were measured using para-nitrophenyl glucose (pNPG) and para-nitrophenyl cellobiose (pNPC), respectively, which are p-nitrophenyl (pNP)-conjugated substrates.

4-1: Endo-β-1,4-Glucanase (EG)

To prepare an enzymatic reaction solution, 5 μL of an enzyme liquid was added to 45 μL of a solution of 2% (w/v) of carboxylmethyl cellulose (CMC) sodium salt (Sigma-Aldrich Fine Chemicals, Co.) in 0.1 M NaAc (Sodium acetate) buffer (pH 5.0), and allowed to react at 50° C. for 30 minutes. After completion of the enzymatic reaction, 50 μL of a copper reagent was added to the reaction solution which was then heated at 1000 for 10 minutes to stop the reaction, and then the amount of reducing sugar produced was measured by the Somogyi-Nelson method. As the unit of enzymatic activity, the amount of enzyme required to release 1 μmol of glucose for 30 minutes under certain conditions was expressed as 1 unit (U).

4-2: β-glucosidase (BG)

To prepare an enzymatic reaction solution (1 mL), 0.1 mL of 10 mM p-nitrophenyl-β-D-glycopyranoside (pNPG, Sigma) and 0.1 mL of an enzyme liquid were added to 0.8 mL of 0.1 M NaAc buffer (pH 5.0), and allowed to react at 50° C. for 15 minutes. Next, 0.1 mL of 2 M $Na_2CO_3$ (sodium carbonate) solution was added to the reaction solution to stop the reaction, and the absorbance at 405 nm was measured to determine the amount of p-nitrophenol produced. As the unit of enzymatic activity, the amount of enzyme required to release 1 μmol of p-nitrophenol for 15 minutes under certain conditions was expressed as 1 unit (U).

4-3: Cellobiohydrolase (CBH)

To prepare an enzymatic reaction solution (1 mL), 0.1 mL of p-nitrophenyl-β-D-cellobioside (pNPC, Sigma) and 0.1 mL of an enzyme liquid were added to 0.8 mL of 0.1 M NaAC buffer (pH 5.0), and allowed to react at 50° C. for 15 minutes. Next, 0.1 mL of 2 M $Na_2CO_3$ (sodium carbonate) solution was added to the reaction solution to stop the reaction, and the absorbance at 405 nm was measured to determine the amount of p-nitrophenol produced. As the unit of enzymatic activity, the amount of enzyme required to release 1 μmol of p-nitrophenol for 15 minutes under certain conditions was expressed as 1 unit (U).

4-4: Results of Measurement of Cellulase Activities

The cellulase activities of *Acanthophysium* sp. KMF001 strain (KCTC 18282P) according to the present invention and the control strains (*Trichoderma reesei*, *Fomitopsis palustris*, and *Aspergillus niger*) were measured. As a result, as shown in Table 8 below, the EG activity of *Acanthophysium* sp. KMF001 strain according to the present invention was similar to that of *Trichoderma reesei* that commercially produces EG. However, the activities of other two cellulases (BGL and CBH) were much higher in *Acanthophysium* sp. KMF001 strain than in the commercial producing strain, and particularly, the CBH activity was 10 times higher in *Acanthophysium* sp. KMF001 strain. In addition, *Acanthophysium* sp. KMF001 strain showed very high cellulase activities compared to *Fomitopsis palustris* and *Aspergillus niger*, generally known as strains that produce cellulases.

TABLE 8

| Classification | endo-β-1,4-glucanase (EG, U/L) | β-glucosidase and (BG, U/L) | cellobiohydrolase (CBH, U/L) |
|---|---|---|---|
| *Acanthophysium* sp. (KCTC 18282P) | 3,820 | 10,960 | 11,140 |
| *Trichoderma reesei* | 4,700 | 8,500 | 1,040 |
| *Fomitopsis palustris* | 860 | No measurement of activities | No measurement of activities |
| *Aspergillus niger* | 240 | 5,740 | 1,500 |

Example 5: Optimization of Strain Culture Conditions for Cellulase Production

In all fungi, cellulases are secreted at different rates depending on various culture conditions, including a carbon source, a nitrogen source, temperature, and pH. Thus, it is important to determine the optimum culture conditions under which strains can easily secrete cellulases. Thus, the optimum culture conditions for cellulase production were investigated while *Acanthophysium* sp. KMF001 strain which showed high cellulase activities in Example 4 was cultured under varying conditions.

5-1: Enzymatic Activities Upon Culture with Various Carbon Sources

The cellulase activities of *Acanthophysium* sp. KMF001 strain cultured in various carbon sources were measured. The carbon sources used were glucose (Duksan), lactose (Duksan), cellobiose (Alfa Aesar), carboxymethyl cellulose (CMC) sodium salt (Fluka), xylan (Sigma), avicel (Fluka), acorn tree woody flour, *Pinus rigida* woody flour, rice-straw and cellulose (Aldrich, about 20 micron). *Acanthophysium* sp. KMF001 strain was subjected to main culture using 2% (w/v) of each of the carbon sources as a substrate, and then the activities of the produced endo-β-1,4-glucanase, β-glucosidase, cellobiohydrolase, and β-1,4-xylosidase were measured, and the proteins were quantified.

TABLE 9

| Carbon source | Enzyme activity (U/mL) | | | | Protein (mg/mL) |
|---|---|---|---|---|---|
| | EG[1] | BGL[2] | CBH[3] | BXL[4] | |
| cellulose | 122.31 ± 6.49 | 5.85 ± 0.55 | 0.60 ± 0.01 | 0.11 | 0.17 ± 0.01 |
| glucose | 1.30 ± 0.87 | 0.40 | 0.10 | 0.19 | 0.59 ± 0.01 |
| lactose | 13.74 | 0.33 ± 0.01 | 0.03 ± 0.01 | 0.05 | 0.08 ± 0.01 |
| cellobiose | 38.77 ± 0.21 | 0.24 | 0.02 | 0.04 | 0.07 |
| CMC | 75.95 ± 2.09 | 0.96 ± 0.02 | 0.17 ± 0.01 | 0.07 | 0.22 ± 0.09 |
| xylan | 30.93 ± 1.68 | 0.73 ± 0.03 | 0.13 ± 0.03 | 0.09 | 0.20 ± 0.01 |
| rice-straw | 214.13 ± 6.91 | 2.56 | 0.49 ± 0.05 | 0.20 ± 0.01 | 0.34 ± 0.03 |
| avicel | 107.94 ± 12.57 | 7.42 ± 0.27 | 0.27 | 0.12 ± 0.01 | 0.15 ± 0.01 |
| acorn | 64.84 ± 0.21 | 0.81 ± 0.01 | 0.17 | 0.12 | 0.22 ± 0.03 |
| rigida | 0.63 ± 0.04 | 0.27 ± 0.01 | 0.02 | 0.05 | 0.10 |
| Control | 0.69 | 0.24 | 0.02 | 0.04 | 0.14 ± 0.05 |

[1]EG: Endo-β-1,4-glucanase
[2]BGL: β-glucosidase
[3]CBH: Cellobiohydrolase
[4]BXL: β-1,4-xylosidase.

Figure 4:
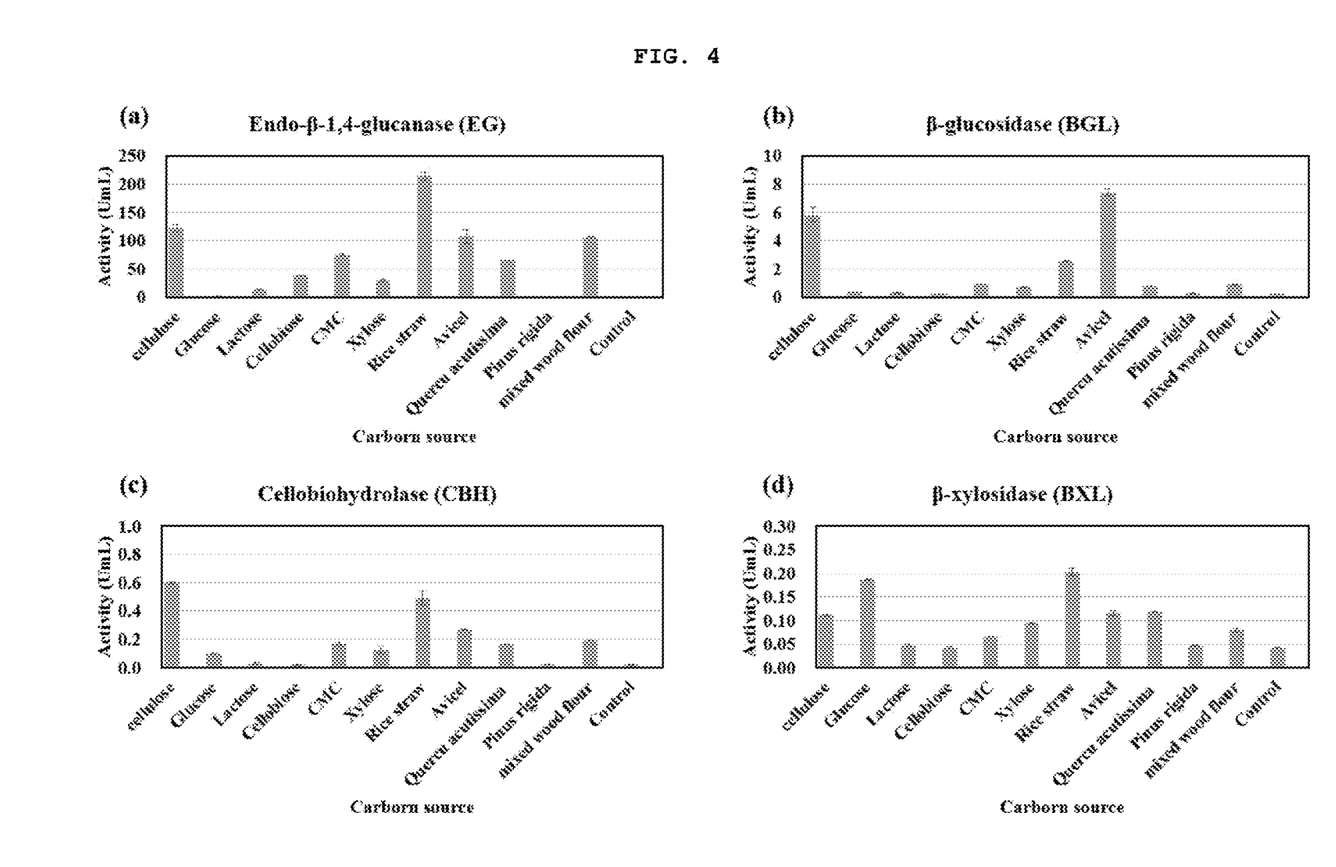
FIG. 4 shows the cellulase activities of *Acanthophysium* sp. KMF001 strain cultured in various carbon sources.

Table 9 above and FIG. 4 show the cellulase activities of *Acanthophysium* sp. KMF001 strain of the present invention, cultured in various carbon sources. As shown therein, the activity of endo-β-1,4-glucanase was the highest in rice-straw (214.13±6.91 U/mL), and was relatively high in cellulose (122.31±6.49 U/mL). The activity of β-glucosidase was the highest in avicel (7.42±0.27 U/mL), and the second highest in cellulose (5.85±0.55 U/mL). The activity of cellobiohydrolase was the highest in cellulose (0.60±0.01 U/mL), and was relatively high in rice-straw (0.49 U/mL). The activity of β-1,4-xylosidase was slightly higher in rice-straw and cellulose than in other carbon sources, but the activity of β-1,4-xylosidase in these carbon sources was not particularly higher than those of other enzymes.

As a result, it is concluded that a carbon source for use in the production of cellulases in *Acanthophysium* sp. KMF001 strain is preferably cellulose in which the activities of all the four enzymes are high.

5-2: Enzymatic Activities Upon Culture with Various Nitrogen Sources

The cellulase activities of *Acanthophysium* sp. KMF001 strain cultured in various nitrogen sources were measured. The nitrogen sources used were yeast extract (Duksan), peptone (Bacto), trypton (Bacto), corn steep powder (Sigma), urea (Duksan), ammonium sulfate (Duksan), potassium nitrate (Duksan), sodium nitrate (Duksan), a 2:8 mixture of yeast extract and peptone, and a 3:7 mixture of yeast extract and trypton. As a carbon source, 2% (w/v) of cellulose (Aldrich, about 20 micron) was used. *Acanthophysium* sp. KMF001 strain was subjected to main culture using 1% (w/v) of each of the nitrogen sources, and then the activities of the produced endo-β-1,4-glucanase, β-glucosidase, cellobiohydrolase and β-1,4-xylosidase were measured, and the proteins were quantified.

TABLE 10

| Carbon source | Enzyme activity (U/mL) | | | | Protein (mg/mL) |
|---|---|---|---|---|---|
| | EG[1] | BGL[2] | CBH[3] | BXL[4] | |
| yeast extract | 65.28 ± 9.64 | 5.54 ± 0.16 | 0.39 ± 0.01 | 0.15 | 0.48 ± 0.06 |
| peptone | 47.95 ± 1.89 | 6.28 ± 0.09 | 0.30 ± 0.01 | 0.12 | 0.29 ± 0.03 |
| trypton | 45.44 ± 3.35 | 3.27 ± 0.07 | 0.20 ± 0.01 | 0.14 | 0.36 ± 0.05 |
| corn steep | 3.20 ± 0.07 | 0.03 | 0.03 | 0.03 | 0.21 |
| urea | 0.54 ± 0.02 | 0.02 | 0.01 | 0.01 | 0.03 |
| ammonium sulfate | 2.49 ± 0.14 | 0.01 | 0.01 | 0.01 | 0.03 |
| potassium nitrate | 3.72 ± 0.04 | 0.01 | 0.01 | 0.00 | 0.03 |
| sodium nitrate | 1.21 ± 0.07 | 0.12 | 0.02 | 0.02 | 0.03 |
| Yeast extract/peptone 0.2/0.8 | 66.17 ± 4.19 | 7.64 ± 0.08 | 0.44 ± 0.02 | 0.16 ± 0.01 | 0.42 |
| trypton/yeast extract 0.7/0.3 | 107.49 ± 9.84 | 12.89 ± 0.18 | 1.15 ± 0.05 | 0.33 | 0.36 |

[1]EG: Endo-β-1,4-glucanase
[2]BGL: β-glucosidase
[3]CBH: Cellobiohydrolase
[4]BXL: β-1,4-xylosidase.

Figure 5:
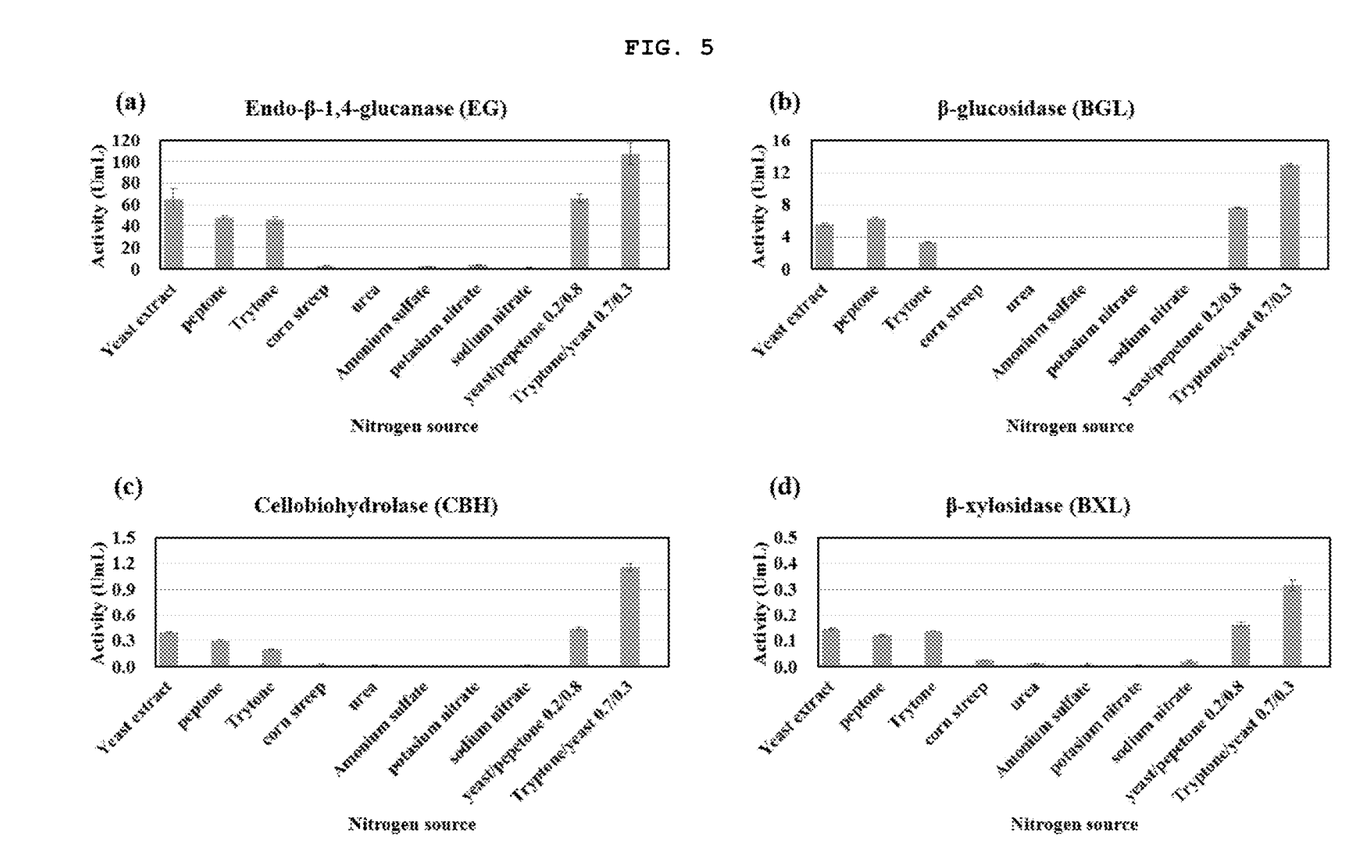
FIG. 5 shows the cellulase activities of *Acanthophysium* sp. KMF001 strain cultured in various nitrogen sources.

Table 10 above and FIG. 5 show the cellulase activities of *Acanthophysium* sp. KMF001 strain of the present invention, cultured in various nitrogen sources. As shown therein, the activity of endo-β-1,4-glucanase was the highest in the 3:7 mixture of yeast extract and tryptone (107.49 U/mL), and was relatively high in the 2:8 mixture of yeast extract and peptone (66.17 U/mL) and yeast extract (65.28 U/mL). The activity of β-glucosidase was the highest in the 3:7 mixture of yeast extract and tryptone (12.89 U/mL), like that of endo-β-1,4-glucanase, and was the second highest in yeast extract (5.54 U/mL). The activity of cellobiohydrolase was the highest in the 3:7 mixture of yeast extract and tryptone (1.15 U/mL). The activity of β-1,4-xylosidase was the highest in the 3:7 mixture of yeast extract and tryptone (0.33 U/mL).

As a result, it could be seen that the use of urea, ammonium sulfate, potassium nitrate, and sodium nitrate did not show the activities of the enzymes, and it is concluded that a nitrogen source for use in the production of cellulases in *Acanthophysium* sp. KMF001 strain is preferably the 3:7 mixture of yeast extract and tryptone in which the activities of all the four enzymes are high.

5-3: Enzymatic Activities at Various pHs

In order to examine the effect of pH on the production of cellulases, the main culture of *Acanthophysium* sp. KMF001 strain was performed at a pH ranging from 4.0 to 7.0. The activities of the produced endo-β-1,4-glucanase, β-glucosidase and cellobiohydrolase were comparatively analyzed.

Figure 6:
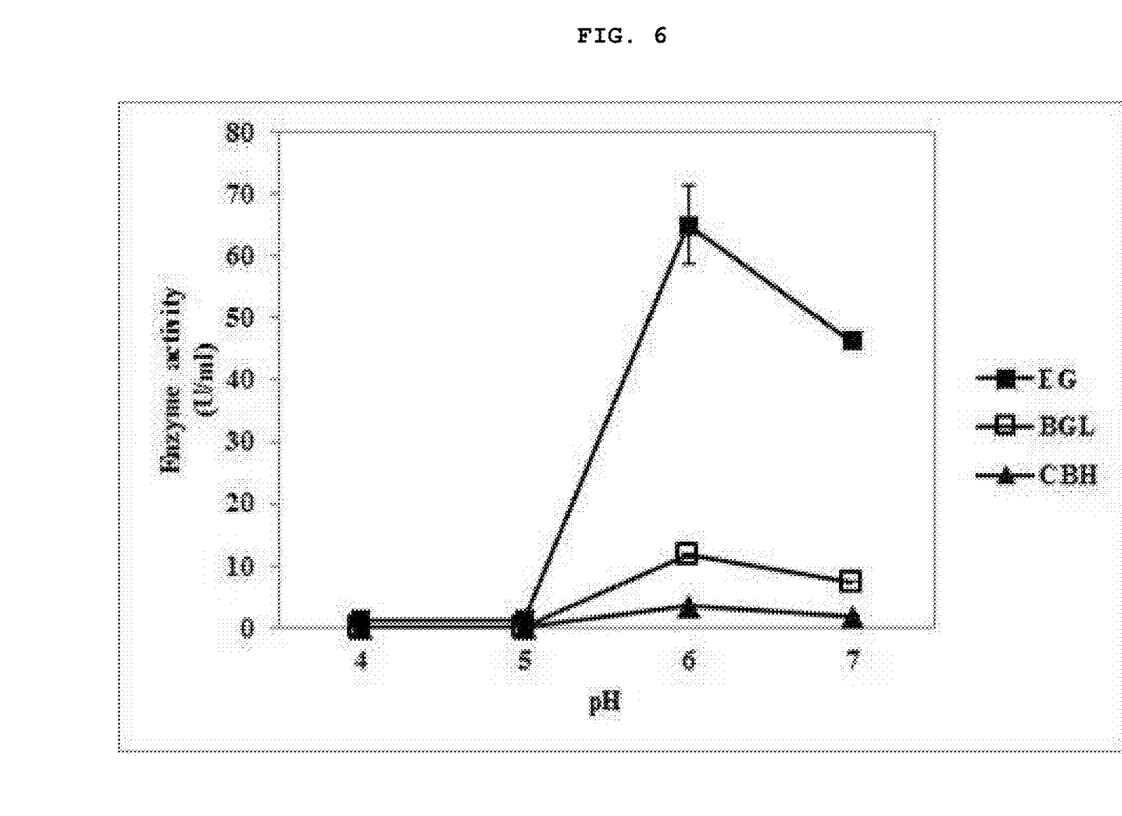
FIG. 6 shows the cellulase activity change of *Acanthophysium* sp. KMF001 strain according to pH change.

As a result, it could be seen that the activities of the enzymes were the highest at pH 6.0. Specifically, at pH 6.0, the activity of endo-β-1,4-glucanase was 65.08 U/mL, the activity of β-glucosidase was 11.73 U/mL, and the activity of cellobiohydrolase was 3.51 U/mL. At pH 7.0, the activity of endo-β-1,4-glucanase was about 71% of the activity shown at pH 6.0, the activity of β-glucosidase was about 64% of the activity shown at pH 6.0, and the activity of cellobiohydrolase was about 52% of the activity shown at pH 6.0. At pHs lower than 6.0, the activities of the enzymes showed a tendency to decrease rapidly. At pH 4.0, the activities of the enzymes decreased by 90% or more. As a result, it is concluded that the optimum pH in the culture of *Acanthophysium* sp. KMF001 strain is pH 6.0 (FIG. 6).

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

DEPOSIT OF MICROORGANISMS

Depository Institution: Korea Research Institute of Bioscience and Biotechnology;
Accession Number: KCTC 18282P
Deposit Date: Apr. 21, 2014.

The invention claimed is:

1. A method for producing cellulase, comprising the steps of:
   (a) culturing *Acanthophysium* sp. KMF001 (KCTC 13124BP) wherein cellulase is produced; and
   (b) recovering the produced cellulase.

2. The method of claim 1, wherein the culture is performed in a medium containing the following: a carbon source selected from the group consisting of cellulose, glucose, lactose, cellobiose, carboxymethyl cellulose (CMC) sodium salt, xylan, rice-straw, cellulose microcrystalline or crystalline cellulose, and acorns; a nitrogen source selected from the group consisting of peptone, yeast extract, tryptone, corn steep powder, urea, a 2:8 mixture of yeast and peptone, and a 7:3 mixture of tryptone and yeast; potassium dihydrogen phosphate ($KH_2PO_4$); potassium hydrogen phosphate ($K_2HPO_4$); and magnesium sulfate ($MgSO_4 \cdot 7H_2O$).

3. The method of claim 1, wherein the culture is performed at a pH of 5.5-6.5 and a temperature of 22 to 28° C.

4. The method of claim 1, wherein the cellulase is selected from the group consisting of endo-1,4-glucanase, β-glucosidase, and cellobiohydrolase.

5. A method for degrading cellulose, the method comprising treating said cellulose with:
   *Acanthophysium* sp. KMF001 strain (KCTC 13124BP) having cellulase activity; or
   the cellulase produced by *Acanthophysium* sp. KMF001 (KCTC 13124BP).

* * * * *

UNITED STATES PATENT AND TRADEMARK OFFICE
CERTIFICATE OF CORRECTION

PATENT NO. : 10,196,621 B2
APPLICATION NO. : 14/930585
DATED : February 5, 2019
INVENTOR(S) : Kim et al.

Page 1 of 1

It is certified that error appears in the above-identified patent and that said Letters Patent is hereby corrected as shown below:

In the Specification

Column 9, Line 45: "1000" should be -- 100° C. --.

Signed and Sealed this
Second Day of April, 2019

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 624
<212> TYPE: DNA
<213> ORGANISM: Artificial Sequence
<220> FEATURE:
<223> OTHER INFORMATION: Acanthophysium sp. KMF001

<400> SEQUENCE: 1
agcggaggaa aagaaactaa caaggattcc cctagtaact gcgagtgaag cgggaaaagc      60
tcaaatttaa aatctggcgg cctctggtcg tccgagttgt agtctggaga agcgttttcc     120
gcgttggacc gtgtacaagt ttcctggaac ggagcgtcat agagggtgag aatcccgtct     180
ttgacacgga tcccaatgct ttgtgatgcg ctctcaaaga gtcgagttgt ttgggaatgc     240
agctcaaaat gggtggtgaa ttccatctaa agctaaatat tggcgagaga ccgatagcga     300
acaagtaccg tgagggaaag atgaaaagca ctttggaaag agagttaaac agtacgtgaa     360
attgttgaaa gggaaacgct tgaagtcagt cgcgtcggcc gggactcagc cttgcattcg     420
cttggtgtac tttccggtcg acgggccagc atcagttttg atcgcgggat aaaggcggag     480
ggaatgtggc tctttcggga gtgttatagc cctctgtcgg atgccgtggt tgggactgag     540
gaactcagca cgcctttatg gccggggttc gcccacgtac ctgcttagga tgctggcgta     600
atggctttaa acgacccgtc ttga                                            624

<210> SEQ ID NO 2
<211> LENGTH: 20
<212> TYPE: DNA
<213> ORGANISM: Artificial Sequence
<220> FEATURE:
<223> OTHER INFORMATION: ITS4 primer
```

```
<400> SEQUENCE: 2
tcctccgctt attgatatgc                                                    20

<210> SEQ ID NO 3
<211> LENGTH: 22
<212> TYPE: DNA
<213> ORGANISM: Artificial Sequence
<220> FEATURE:
<223> OTHER INFORMATION: ITS5 primer

<400> SEQUENCE: 3
ggaagtaaaa gtcgtaacaa gg                                                 22
```